(12) United States Patent
Oliver

(10) Patent No.: US 7,022,081 B2
(45) Date of Patent: Apr. 4, 2006

(54) HEAT SEALABLE TRANSDUCER SHIELD AND METHOD OF APPLICATION

(75) Inventor: Nelson H. Oliver, Sunnyvale, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 224 days.

(21) Appl. No.: 10/644,183

(22) Filed: Aug. 20, 2003

(65) Prior Publication Data

US 2005/0043624 A1    Feb. 24, 2005

(51) Int. Cl.
*A61B 8/14* (2006.01)

(52) U.S. Cl. .................................... 600/459

(58) Field of Classification Search ........ 600/437–472; 73/625, 626, 644; 128/916; 29/25.35; 310/330–337
See application file for complete search history.

(56) References Cited

U.S. PATENT DOCUMENTS 4,961,347 A * 10/1990 Arakawa et al. .............. 73/644

* cited by examiner

*Primary Examiner*—Ali Imam

(57) ABSTRACT

Transducers and methods of manufacturing transducers with at least one of environmental and electromagnetic protection are provided. Diced ultrasonic transducer stacks are covered with a shield layer or film. The shield layer is bonded to the transducer stack without adhesive. For example, a heat sealable amorphous surface is used to bond the shield layer to the ultrasound stack. The shield layer forms an environmental and/or electromagnetic barrier. Since adhesive is not used for bonding the shield layer, the kerfs are uniformly air filled.

24 Claims, 3 Drawing Sheets

HEAT SEALABLE TRANSDUCER SHIELD AND METHOD OF APPLICATION

BACKGROUND

The present invention relates to ultrasound transducer barrier shields. In particular, shields for providing one or both of environmental and electrical protection for a transducer are provided.

To provide electromagnetic interference and environmental-chemical isolation, a thin shielding layer or film is positioned over ultrasound transducer elements, beneath the lens or window. For example, ultrasound transducers adapted to be inserted within the patient, such as a catheter-based transducer, are so shielded. Typically, a polyethylene-terephthalate (PET) film is bonded to a transducer stack with a castable elastomer, such as siloxane or urethane.

Transducers typically include an array of elements. Each transducer element is separated from other transducer elements by a kerf. When the shield layer is bonded, the kerfs are filled with the bonding adhesive. However, the directivity or acoustic roll off from each individual transducer element is not as good when the kerfs are filled with the liquid or cured solid adhesive as opposed to being filled with air or other gas.

To keep the kerfs filled with air, small amounts of adhesive may be used to bond the shield layer to the transducer stack. As a result, most of any given kerf is filled with air. However, uneven, partial fill, or a meniscus of the adhesive material is typically formed at the top portion of one or more of the kerfs. Different kerfs may have different amounts of partial fill; (i.e., irreproducible and variable degrees of kerf filling result). The element-to-element variability changes the acoustic directivity on a random basis. As a result, the acoustic directivity is neither as good nor as uniform as that provided by fully air- or gas-filled kerfs.

BRIEF SUMMARY

The present invention is defined by the following claims, and nothing in this section should be taken as a limitation on those claims. By way of introduction, the preferred embodiments described below include transducers and methods of manufacturing transducers with at least one of environmental and electromagnetic protection. Diced ultrasonic transducer stacks are covered with a shield layer. The shield layer is bonded to the transducer stack without liquid adhesive. For example, a heat sealable amorphous-polymer surface is used to bond the shield layer to the ultrasound stack. The shield layer forms an environmental and/or electromagnetic barrier. Since liquid adhesive is not used for bonding the shield layer, the kerfs are more completely and uniformly air filled.

In a first aspect, an ultrasound transducer with at least one of environmental and electromagnetic protection is provided. Two transducer elements are positioned adjacent to each other. A kerf separates the transducer elements. A shield layer is positioned over at least portions of the two elements and the kerf. A bond holding the shield layer adjacent to the portions is free of adhesive.

In a second aspect, an ultrasound transducer is provided with at least one of environmental and electromagnetic protection. Two transducer elements are separated by a kerf. A shield layer is provided over portions of the transducer elements and the kerf. The bond holding the shield layer adjacent to the portions is a heat seal or fusion bond.

In a third aspect, a method for manufacturing an ultrasound transducer with at least one of environmental and electromagnetic protection is provided. A shield layer, a transducer element and an electrode are stacked. The shield layer is bonded to a portion of the stack with a heat seal or fusion bond.

In a fourth aspect, a method for manufacturing an ultrasound transducer with at least one of environmental and electromagnetic protection is provided. A shield layer, a transducer element and an electrode are stacked. The shield layer is heat sealed to a portion of the stack.

Further aspects and advantages of the invention are discussed below in conjunction with the preferred embodiments.

BRIEF DESCRIPTION OF THE DRAWINGS

The components and the figures are not necessarily to scale, emphasis instead being placed on illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
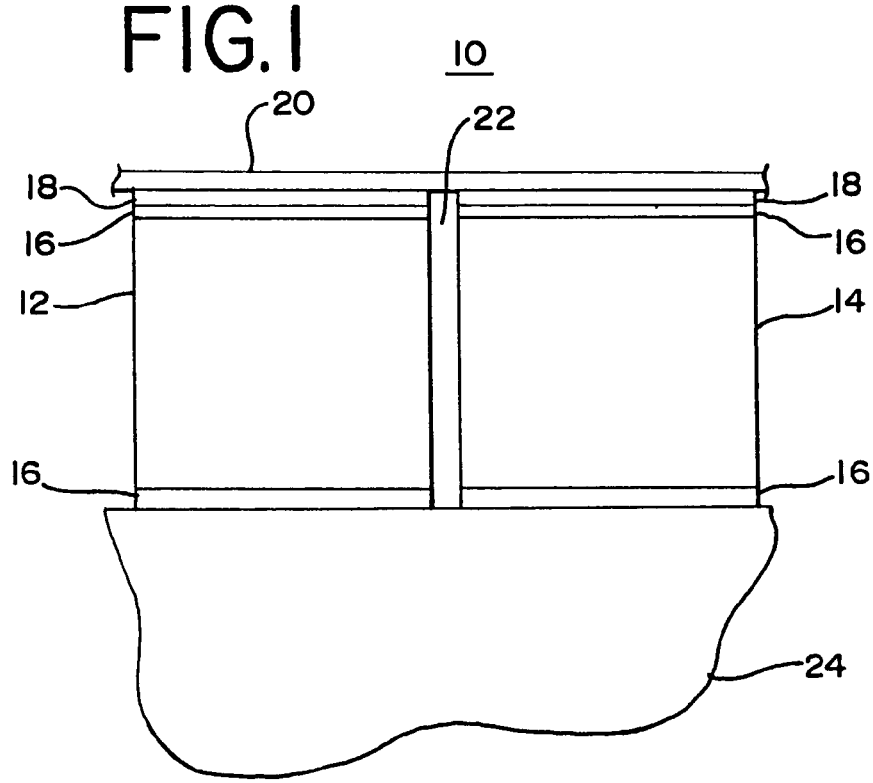
FIG. 1 is a cross section view of one embodiment of a transducer stack with a shield layer bonded without liquid adhesive.

FIG. 1 shows two transducer elements 12 and 14 of an ultrasound transducer 10 with a shield layer 20 for environmental and/or electromagnetic protection in one embodiment. The ultrasound transducer is an array of one or more elements. For example, 64, 128, or 256 elements are provided. The transducer 10 is adapted for use external to a patient or internal to a patient, such as a catheter, transesophageal probe or endocavity transducer. The transducer 10 is sized and materials selected for use as a medical diagnostic imaging transducer. In alternative embodiments, the transducer 10 is adapted for materials testing at ultrasound or other acoustic frequencies.

One embodiment of the transducer 10 includes at least two transducer elements 12 and 14. Each of the transducer elements 12, 14 contains a piezoelectric (PZT) ceramic, PZT composite material, microelectromechanical device, capacitive membrane ultrasound transducer, or other now known or later developed materials for transducing between acoustic and electrical energies.

A pair of electrodes 16 is provided in each of the elements 12 and 14. As used herein, element is either just the PZT or the column of PZT and matching layers. In one embodiment, the bottom electrodes 16 are used for transceiving signals and the top electrodes 16 act as a ground. The top electrodes 16 are positioned adjacent to the PZT, but maybe spaced from the elements by one or more matching layers 18. In one embodiment, a triaxial ground is provided as a ground plane on an upper surface of the shield layer 20. As shown in FIG.

1, a matching layer 18 is provided for each of the transducer elements 12, 14. In alternative embodiments, none, two or more matching layers 18 are provided. The transducer elements 12 and 14 are stacked on a backing block 24. The backing block 24 includes acoustically attenuative materials for absorbing ultrasound energy.

The transducer elements 12, 14 are separated by a kerf 22. The kerf 22 is of various sizes or widths. In one embodiment, the kerf 22 is the width associated with a dicing saw, such as about 100 μm. The kerf 22 separates the one element 12 from the other transducer element 14. As shown, the kerf 22 typically extends throughout the entire depth of the elements 12 and 14 and into the backer 24. In alternative embodiments, the kerf 22 extends through only a portion of the depth of the elements 12 and 14. The kerf 22 also separates the matching layers 18 of different elements and may optionally separate the electrodes 16 for each of the elements 12, 14.

The shield layer 20 is usually polyester or polyamide material. For example, a PET film is used, such as Mylar.® In alternative embodiments, a polyamide film, such as Kapton,® is used, but any of various now known or later developed barrier materials may be used. The shield layer 20 is 0.5 mils to 12 mils in thickness, but greater or lesser thicknesses may be provided. The shield layer 20 is positioned on at least portions of the two transducer elements, 12, 14 and the kerf 22. In one embodiment, the shield layer 20 is positioned over the entire upper surface of the transducer elements 12 and 14 and over the entire width of the kerf 22. For example, the shield layer 20 is positioned as a single film over the entire array of transducer elements. While shown as just on the upper surface in FIG. 1, the shield layer 20 may also extend around to the sides and/or back of the transducer array 10.

The shield layer 20 includes a bond holding the shield layer 20 affixed to the elements 12 and 14. In one embodiment, the shield layer 20 is bonded to the matching layer 18, but alternatively may be bonded to other transducer stack components. The bond is sufficient to keep the shield layer 20 from delaminating throughout the life of the transducer.

The bond holding the shield layer 20 adjacent to the transducers 12 and 14 is free of adhesive in one embodiment. For example, silicone, epoxy or other resins are not used for bonding the shield layer 20. In one embodiment, the shield layer 20 is a polyester film with an amorphous surface. For example, a lower surface or surface adjacent to the transducer element 12 and 14 is an amorphous polymer. The other (upper) surface is either also amorphous or has a crystalline structure. The amorphous surface is a surface layer fabricated such that the structural transition to the crystalline state occurs at a lower temperature than the melting point or softening point of the film. While a coextruded amorphous/crystalline PET film that is known as APET/CPET is one example, other films and shield materials for implementing a heat sealable or fusion bond may be provided. The amorphous surface of the shield layer 20 is operable to bond the shield layer 20 to the transducer 10. By application of heat and/or pressure, the amorphous surface undergoes an amorphous-to-crystalline restructuring to create a bond. As a result, heat may be used to cause the amorphous-to-crystalline transition, and so effect the resulting bond. Since the bond is free of adhesive, the kerf 22 is filled with gas, such as air, and is free of adhesive.

In an alternative embodiment, the matching layer 18 has a heat-sealable amorphous-polymer surface, and undergoes the amorphous-to-crystalline transition to generate a bond with the shield layer 20. The bond generated between the shield layer 20 and the matching layer 18 is also free of adhesive. For example, a heat sealable film, such as an APET/CPET (amorphous PET/crystalline PET) is used as part of a low impedance matching layer 18 in the transducer stack. APET/CPET films are available in 0.5 mils to 12 mils thickness and provide usefully low impedances for matching networks. In alternative embodiments, different thicknesses are provided, such as by grinding the crystalline or CPET surface of the film to a desired thickness or profile. When bonded as part of the matching layer network, the amorphous or APET surface of the film is stacked to face away from the transducer elements 12 and 14. The crystalline or CPET surface is epoxy bonded or otherwise connected with the electrodes 16 and/or the transducer elements 12, 14. The shield layer 20 is then heat sealed or fusion bonded to the matching layer 18. For example, the shield layer 20 is a polyester such as PET, polyamide, or other film capable of heat sealing or fusion bonding via the amorphous surface of the outermost matching layer 18. Where the kerf 22 is formed after the matching layer 18 is bonded to the transducer elements 12 and 14, and before bonding of the shield layer 20, the amorphous surface provides a heat sealable bond free of adhesive. As a result, the kerf 22 is maintained free of adhesive material.

Figure 3:
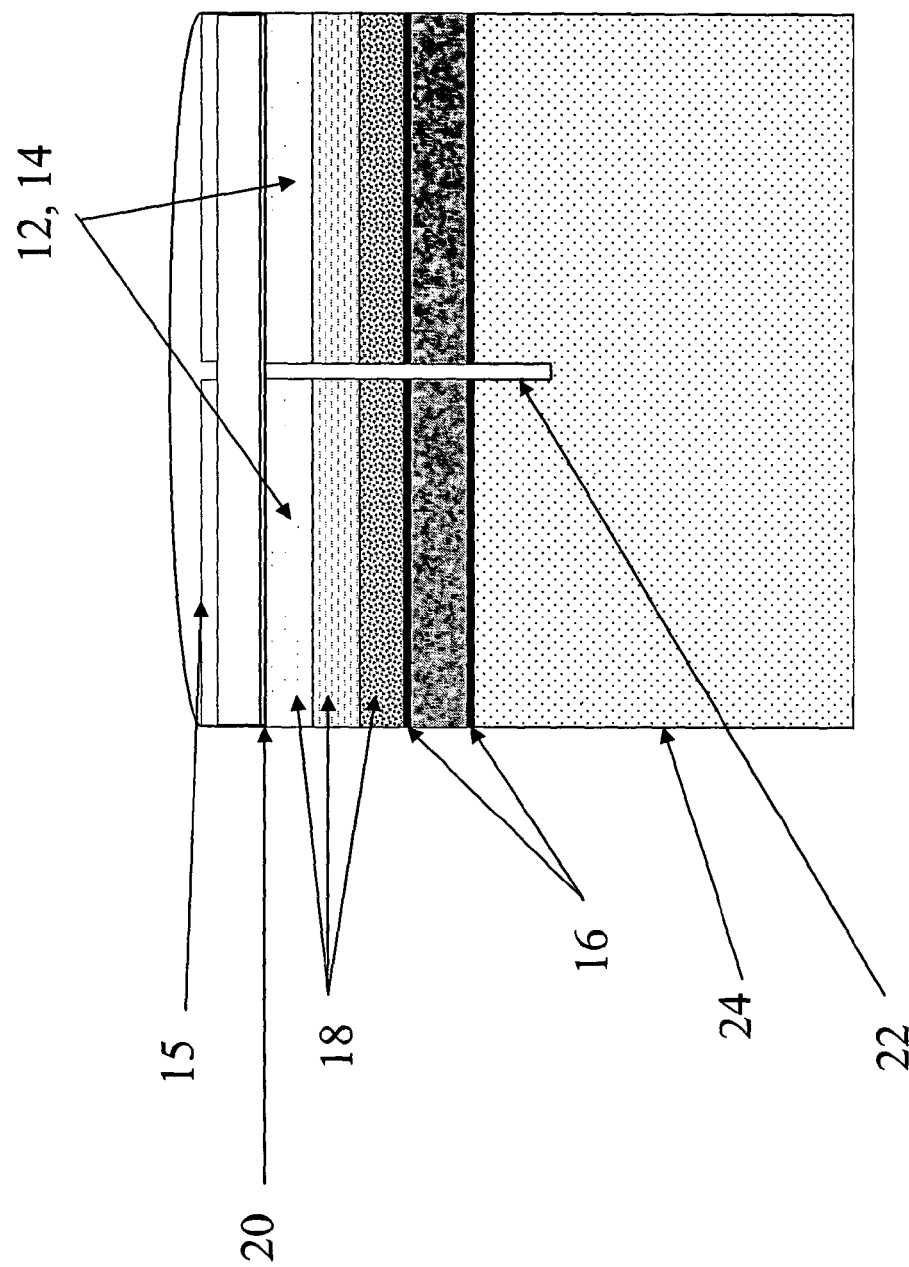
FIG. 3 is a cross section view of another embodiment of a transducer stack with a shield layer bonded without liquid adhesive.

FIG. 3 shows another embodiment of a transducer 10 with the shield layer 20. Three matching layers 18 are used with a lens or window 15 over the matching layers. The elements 12, 14 are labeled as stacks of materials including the PZT.

Figure 2:
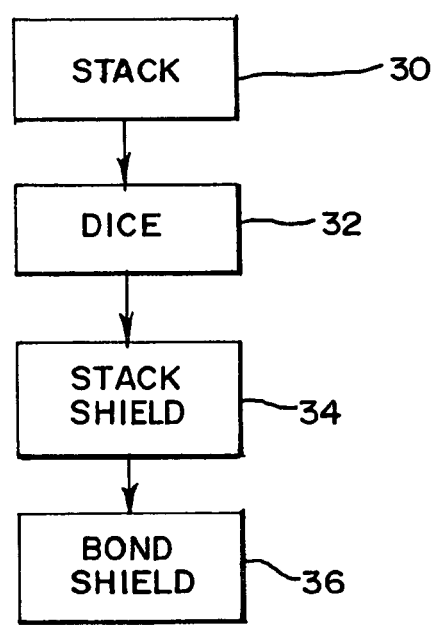
FIG. 2 is a flow chart diagram of one embodiment of a method of manufacturing a transducer stack with a shield layer bonded without liquid adhesive.

FIG. 2 shows one embodiment of a flow chart representing a method for manufacturing an ultrasound transducer with a shield imparting at least one of environmental and electromagnetic protection. In act 30, a shield layer and a transducer element are stacked. Stacking also includes any other transducer components. For example, signal traces, transducer elements and matching layers are all stacked as films, plates or other structures on a backing block. The stacked transducer, electrode, matching layer and other materials are formed as sheets sized and shaped as appropriate for forming the entire array or a portion of the array of the transducer. In alternative embodiments, individual elements of the array are stacked separately.

The stacked materials are then bonded together, such as through an epoxy bond with heat and pressure. One or more of the materials may be separately stacked, such as by depositing electrodes onto the transducer material. The transducer material and the deposited electrodes are then stacked with other materials of the transducer. In one embodiment, liquid bonding materials, such as silicone or epoxy, hold the materials together. In alternative embodiments, other now known or later developed bonding techniques are used. The stack is then cured, such as through room temperature or oven curing.

In one embodiment, one or more matching layers are stacked with the transducer material. An upper or top matching layer includes an amorphous polymer surface facing away from the transducer materials. For example, a heat sealable film, such as DuPont Melinex® APET/CPET, is used as part of or all of a low impedance matching layer. The amorphous surface is left free, facing away from the stack. The crystalline surface of the matching layer may be treated with oxygen plasma prior to stacking to facilitate bonding. The crystalline PET surface is epoxy bonded to one or multiple materials of the stack. In alternative embodiments, the matching layer is any of now known or later developed matching layer materials, such as a PET film, and the shield layer 20 that is not mounted during stack bond has an amorphous surface facing towards the transducer element.

In act 32, the transducer material is diced. The dicing occurs prior to stacking the shield layer in act 34. Using a dicing saw, etching, or other now known or later developed techniques, the transducer material is separated into one or more elements. The dicing forms the kerfs, a groove, space, or volume separating the transducer materials of different elements from other elements. Since the dicing occurs after bonding the stack, the kerfs are created free of adhesive. Adhesive may form a portion of the walls of the kerf after dicing but is not within the kerf.

After the dicing of act 32, the shield layer is stacked onto the transducer in act 34. In one embodiment where the matching layer 18 includes the amorphous surface, the shield layer 20 is placed adjacent to the transducer stack. The shield layer may or may not be treated with oxygen plasma on the downward surface or surface in contact with the matching layer. The outer surface of the matching layer of each of the individual components or elements formed by dicing includes an amorphous polymer surface. For example, a one dimensional array of elements has a corresponding array of matching layers, appearing as narrow strips of exposed amorphous surface of the matching layers atop each of the elements. The shield layer, such as a PET film, is brought into contact with the amorphous polymer surface of the matching layer to effect bonding.

In one embodiment, the surface of the shield layer 20 positioned away from the transducer elements 12 and 14 includes metallization, such as for use as a ground plane or EMI shield. The metallization may be added at later acts in alternative embodiments. Metallization or electrodes may be provided on other materials in yet other embodiments.

In the embodiment where the shield layer 20 includes the amorphous polymer surface, the matching layer 18 or other materials of the stack is treated, such as with an oxygen plasma treatment. In other alternative embodiments, no surface treatment is provided prior to heat sealing. The amorphous surface of the shield layer 20 is positioned adjacent to or in contact with the transducer elements to effect bonding.

In act 36, the shield layer is bonded to the stack. For example, the shield layer 20 covers the entire array and is bonded to the entire array of elements. In alternative embodiments, the shield layer 20 is bonded to only a portion of one or more elements. The shield layer 20 is bonded to the stack with a heat seal or a fusion bond. A heated pad or hot bar is applied to the outer surface of the shield layer 20 while it is in contact with the transducer elements 12, 14. In one embodiment, the hot pad is applied with a greater pressure than atmospheric pressure, such as 40 psi. Other pressures may be used. The hot pad is kept at about 150° Celsius, but other temperatures may be used. The hot pad is applied for approximately one second, but other amounts of time may be used. Application of the hot pad acts to heat seal the shield layer to the stack. By applying heat to the amorphous polymer surface, the amorphous surface transitions to a crystalline structure. The thermal transition to a crystalline polymer structure results in a bond between the initially amorphous surface and another surface. For example, the amorphous-polymer surface of the shield layer 20 is bonded to a matching layer or other portion of the transducer stack. As another example, the amorphous-polymer surface of a matching layer 18 is bonded to the shield layer 20. As yet another example, the amorphous-polymer surface of the shield layer 20 is bonded to the amorphous-polymer surface of a matching layer 16. Various peel strengths may result from heat seal bonds. In one example, the peel strength is about 500 g/in.

By using the amorphous polymer surface to effect a heat-seal bond, the bonding region is free of liquid adhesive. The bonding is free of any added adhesive. As a result of bonding the shield layer without liquid adhesive, bonding material, such as cured liquid adhesive, is not positioned within the kerf 22. The kerf 22 is maintained free of undesired adhesive materials. The kerf 22 is filled with gas, such as air, beneath the shield layer 20. By minimizing or avoiding liquid or solid adhesive materials within the kerf 22, consistent and optimal acoustic directivity performance is provided. The shield layer 20 acts to cover the kerfs 22 and prevent chemical or other environmental substances from entering the kerf and altering performance. The shield layer 20 also provides electromagnetic and environmental protection to the transducer 10, for example, providing a metallized shield layer as a ground plane to prevent EMI.

Figure 4:
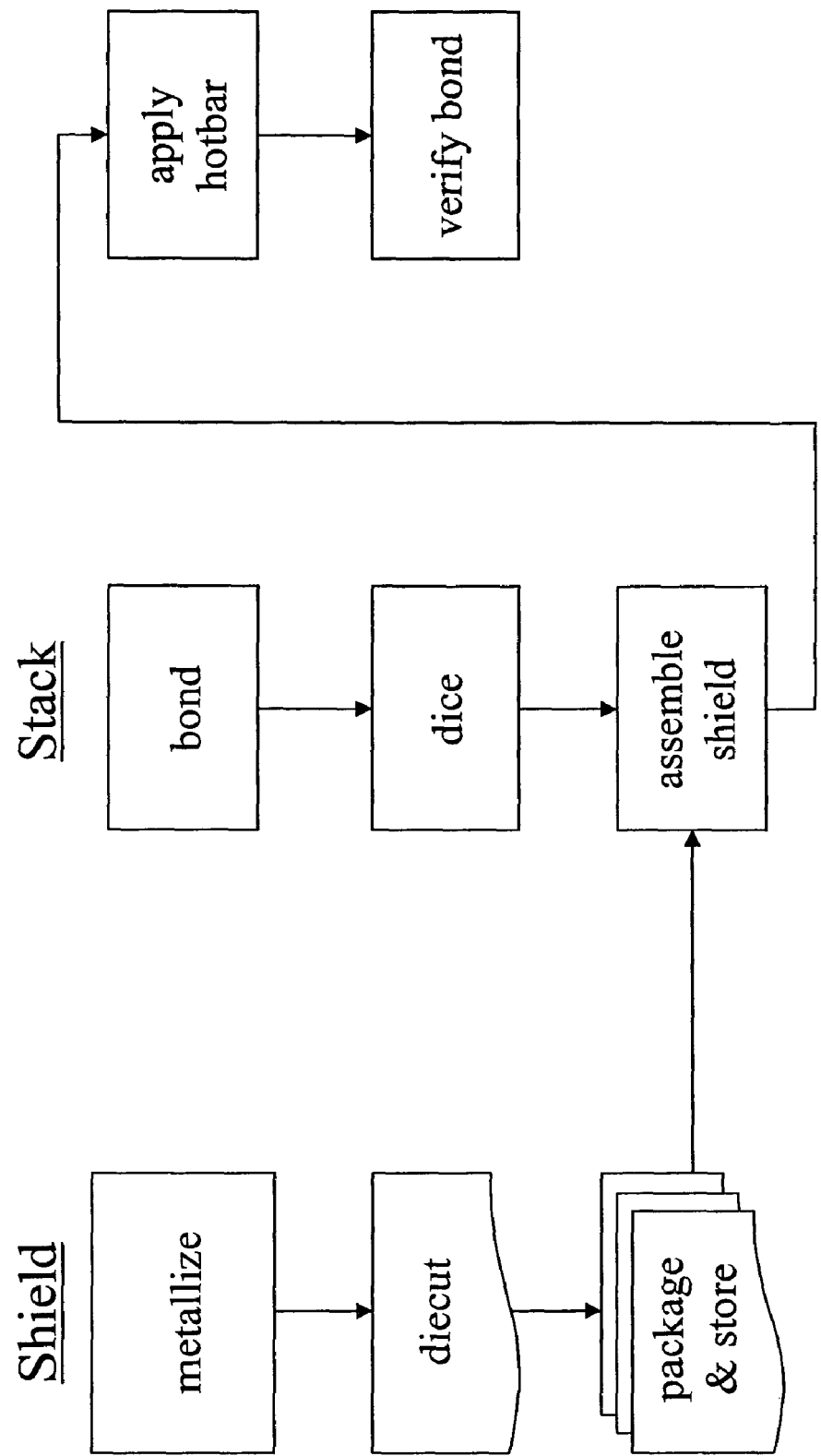
FIG. 4 is a flow chart diagram of another embodiment of a method of manufacturing a transducer stack with a shield layer bonded without liquid adhesive.

FIG. 4 shows a flow chart of one embodiment of the method of FIG. 2 in more detail. The shield processing and stack processes are shown separately prior to assembling the shield with the stack. The bond resulting from the heat seal is verified to assure quality.

In an alternative embodiment, a nearly instantaneous bond is provided without liquid adhesive. For example, a solid adhesive or dried adhesive is provided for performing an instantaneous bond. In one embodiment, a two part no-mix methacrylate coating is used. The glue or adhesive part is dried on the shield layer 20 or on the transducer stack. A catalyst is then sprayed on the other of the transducer stack or shield layer. When placed in contact, an instantaneous bond is provided by the interaction of the catalyst with the dried adhesive. This non-liquid bond is less likely to result in adhesive materials entering the kerf 22. Some adhesive material may be provided as a dried or cured adhesive on the shield layer 20 above the kerf 22. Since the adhesive is dried or cured prior to stacking, the adhesive is consistently positioned across multiple kerfs.

While the invention has been described above by reference embodiments, in should be understood that many changes and modifications can be made without departing from the scope of the invention. For example, any of various materials operable to provide a heat sealed bond, fusion bond, a bond free of liquid adhesive, and/or other bonds may be provided.

It is therefore intended that the foregoing detailed description be regarded as illustrative rather than limiting, and that it be understood that it is the following claims, including all equivalents, that are intended to define the spirit and the scope of this invention.

I claim:

1. An ultrasound transducer with a shield imparting at least one of environmental and electromagnetic protection, the transducer comprising:
   a first transducer element;
   a second transducer element adjacent to the first transducer element, a first kerf separating the first transducer element from the second transducer element; and
   a shield layer over at least portions of the first transducer element, the second transducer element and the kerf, a bond, holding the shield layer adjacent to the portions of the first transducer element and the second transducer element, being free of cured liquid adhesive.

2. The transducer of claim 1 wherein the shield layer comprises a heat sealable film with an amorphous surface, the amorphous surface operable to bond the shield layer adjacent to the portions of the first transducer element and the second transducer element.

3. The transducer of claim 1 wherein the bond comprises a fusion bond.

4. The transducer of claim 1 wherein the bond comprises a heat sealed bond.

5. The transducer of claim 1 wherein the kerf comprises gas without adhesive.

6. The transducer of claim 1 further comprising a matching layer, the matching layer having an amorphous-to-crystalline thermal transition in a polymer to bond to the shield layer.

7. The transducer of claim 1 further comprising the shield layer utilizing an amorphous-to-crystalline thermal transition in a polymer to bond to the matching layer.

8. An ultrasound transducer with at least one of an environmental and electromagnetic protection, the transducer comprising:
   a first transducer element;
   a second transducer element adjacent to the first transducer element, a first kerf separating the first transducer element from the second transducer element; and
   a shield layer over at least portions of the first transducer element, the second transducer element and the kerf, a bond holding the shield layer adjacent to the portions of the first transducer element and the second transducer element being of a heat seal bond.

9. The transducer of claim 8 wherein the shield layer comprises a polyester with an amorphous surface, the amorphous surface operable to bond the shield layer adjacent to the portions of the first transducer element and the second transducer element.

10. The transducer of claim 8 wherein the bond comprises an amorphous-to-crystalline heat seal bond.

11. The transducer of claim 8 wherein the kerf comprises air without adhesive.

12. The transducer of claim 8 further comprising a matching layer, wherein one of the matching layer and the shield layer utilizes an amorphous-to-crystalline thermal transition to heat seal or fusion bond to the other of the shield layer and the matching layer.

13. A method for manufacturing an ultrasound transducer with at least one of environmental and electromagnetic protection, the method comprising:
   (a) stacking at least a shield layer and transducer material;
   (b) bonding a polymer surface of the shield layer to a portion of the stack of (a) with a heat seal bond.

14. The method of claim 13 wherein (b) comprises heat sealing the shield layer to a portion of the stack.

15. The method of claim 13 wherein (b) comprises bonding free of adhesive.

16. The method of claim 13 wherein (a) comprises:
   (a1) stacking the transducer material and electrode material;
   (a2) dicing the transducer material and the electrode material; and then
   (a3) performing (b) without liquid bonding material.

17. The method of claim 16 wherein (b) comprises bonding the shield layer without positioning bond material within a kerf between adjacent elements formed by (a2).

18. The method of claim 13 wherein (a) comprises stacking a matching layer with the polymer surface being an amorphous polymer surface facing away from the transducer material;
   further comprising:
   (c) dicing the transducer material prior to stacking the shield layer;
   wherein (a) comprises stacking the shield layer on the matching layer after (c) and where (b) comprises applying heat to the amorphous polymer surface.

19. The method of claim 13 wherein (a) comprises stacking the transducer element;
   further comprising:
   (c) dicing the transducer material;
   wherein (a) comprises stacking the shield layer after (c), the shield layer having the polymer surface facing towards the transducer material and wherein (b) comprises applying heat to the amorphous polymer surface.

20. The method of claim 13 further comprising:
   (d) dicing the transducer element prior to stacking the shield layer;
   wherein kerfs from the dicing of the transducer material are maintained free of liquid adhesive and free of solid adhesive beneath the shield layer.

21. A method for manufacturing an ultrasound transducer with at least one of environmental and electromagnetic protection, the method comprising:
   (a) stacking at least a shield layer and transducer material;
   (b) heat sealing the shield layer to a portion of the stack of (a);
   (c) forming kerfs within the transducer material;
   wherein (a) comprises stacking the shield layer over the kerfs, the kerfs filled with a gas and free of both of solid adhesive and liquid adhesive.

22. The method of claim 21 wherein (b) comprises bonding the shield layer to the portion with an amorphous polymer surface on the shield layer.

23. The method of claim 21 wherein (b) comprises bonding the shield layer to the portion with an amorphous polymer surface on the portion.

24. The method of claim 21 wherein (b) comprises bonding the shield layer to the portion with amorphous polymer surfaces on both the shield layer and the portion.

* * * * *